(12) United States Patent
Strecker

(10) Patent No.: US 6,221,100 B1
(45) Date of Patent: *Apr. 24, 2001

(54) ENDOPROSTHESIS PERCUTANEOUSLY INPLANTABLE IN THE BODY OF A PATIENT

(76) Inventor: Ernst Peter Strecker, Vierordstrasse 7a, 76228 Karlsruhe (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/942,656

(22) Filed: Oct. 2, 1997

Related U.S. Application Data

(63) Continuation of application No. 08/500,447, filed on Jul. 10, 1995, now abandoned.

(30) Foreign Application Priority Data

Jul. 9, 1994 (DE) .................................................. 44 24 242

(51) Int. Cl.[7] .............................................................. A61F 2/06
(52) U.S. Cl. .............................................................. 623/1.22
(58) Field of Search ............................... 623/1, 11, 12, 623/1.15, 1.2, 1.22

(56) References Cited

U.S. PATENT DOCUMENTS

| 4,732,152 | 3/1988 | Wallsten et al. ........................ 623/1 |
| 5,776,161 | * 7/1998 | Globerman .............................. 623/1 |
| 5,800,456 | * 9/1998 | Maeda et al. ............................ 623/1 |
| 5,800,508 | * 9/1998 | Goicoechea et al. .................... 623/1 |
| 5,800,519 | * 9/1998 | Sandock ................................... 623/1 |

FOREIGN PATENT DOCUMENTS

| 4137857 | 11/1988 | (DE) . |
| 0183372 | 6/1986 | (EP) . |
| 0221570 | 5/1987 | (EP) . |
| 0292587 | 11/1988 | (EP) . |
| 0364787 | 4/1990 | (EP) . |
| 0423916 | 4/1991 | (EP) . |
| 0556850 | 8/1993 | (EP) . |
| 0578998 | 1/1994 | (EP) . |
| 0645125 | 3/1995 | (EP) . |
| WO 90/05554 | 5/1990 | (WO) . |
| WO 93/06781 | 4/1993 | (WO) . |
| WO 93/13825 | 7/1993 | (WO) . |
| WO 94/03127 | 2/1994 | (WO) . |

* cited by examiner

Primary Examiner—David H. Willse
Assistant Examiner—Suzette J. Jackson
(74) Attorney, Agent, or Firm—Hamilton, Brook, Smith & Reynolds, P.C.

(57) ABSTRACT

An endoprosthesis is percutaneously implantable in the body of a patient by means of a catheter, this endoprosthesis being changeable from a small lumen during insertion to a larger lumen conforming to the functional position. This implant has a hose-like netting produced from at least one elastic filament, such netting having the structure of a wire mesh fence with meshes forming polygons, wherein the filaments each grip around each other in the corner points of the meshes following each other in the direction of the longitudinal axis of the prosthesis. According to an alternative embodiment, the endoprosthesis is a hose-like netting produced from elastic filament, such netting having the structure of a wire mesh fence with meshes forming polygons, wherein the meshes have connection zones with two filaments twisted around each other, such connection zones in each case extending in the longitudinal direction of the prosthesis.

22 Claims, 4 Drawing Sheets

ENDOPROSTHESIS PERCUTANEOUSLY INPLANTABLE IN THE BODY OF A PATIENT

This is a continuation of application Ser. No. 08/500,447 filed on Jul. 10, 1995, now abandoned.

BACKGROUND OF THE INVENTION

1. Field of the Invention

The present invention relates to an endoprosthesis percutaneously implantable by means of a catheter in the body of a patient, particularly in tubular vessels or organs, said endoprosthesis being designed in the form of an oblong, hollow body and, upon placement in the correct position during implantation, being changeable from a small lumen during insertion into a larger lumen conforming to its functional position.

2. The Prior Art

Prostheses capable of being inserted percutaneously and changeable in their lumen are known. They serve the purpose of opening or widening vascular lumina either by mechanical expansion by means of known balloon catheters from a small to a larger lumen, or such a prosthesis expands by itself after prior compression by spring force prior to the implantation, due to the initial stress produced in the spring during the compression.

EP-A-0,292,587 describes an endoprosthesis that is received on a balloon catheter and expandable by dilation, as well as detachable from the catheter and placed in a vessel. This prosthesis is a "stent" manufactured by knitting or crocheting from metal or plastic thread material into the form of a hose-like hollow body, in connection with which the individual stitches consist of loosely meshing loops. During expansion, widening, due to dilation of the balloon of the catheter, the meshing loops undergo plastic deformation, and the expanded prosthesis thus remains in its expanded position.

Self-expanding stents have been described in the prior art, for example in EP-A-0,183,372, U.S. Pat. No. 4,732,152 and DE-OS 4,137,857. Prior to their implantation, these prostheses are compresses against inherent spring return forces to a reduced cross section, inserted into the body in the compressed state, and, upon placement in the correct position, expand again in the respective vessel or hollow body of the patient's body due to cancellation of the force of retention, and are fixed thereby.

The endoprosthesis described in EP-A-0,183,372 is one which, for the purpose of implantation, is compressed to a reduced cross section and then pushed in the compressed state by means of a pusher through a catheter previously inserted in the vessel, until it is positioned in the right position in the vessel. Such advancing of the prosthesis through the catheter requires a considerable expenditure of force because the displacement is counteracted by high frictional forces.

A woven and elastically designed endoprosthesis has been described earlier in U.S. Pat. No. 4,732,152, which, in the compressed state, is kept together by a double cover, which is closed at the distal end. This cover is pulled back from the folded prosthesis in the same way as a stocking is pulled from the foot of a wearer. For the purpose of avoiding the friction occurring in this process, liquid may be filled in between the two leaves of the cover. However, this system, which seems to be initially suitable due to the reduction of the frictional resistances, is very complicated with respect to handling.

DE-OS 4,137,857 describes a hollow body. This prosthesis is compressed against the action of resetting spring forces to a cross section that is reduced versus the widened functional position, and kept in this position by means of a mountable covering. After the covering has been mounted, the prosthesis automatically widens to a cross section conforming to the functional position. The covering, which may be a meshwork approximately in the form of a round crocheting, extends over the entire length of the prothesis and consists of at least one through-extending filament and one pull-up line. The prosthesis, which is kept in a radially compressed position by the covering, can be advanced, for example on a guide wire, or also rigidly received axially on the end of a probe or catheter.

Finally an endoprosthesis is known, for which no documentation is available in the form of a published reference made from a memory alloy. This endoprosthesis is an oblong hollow body with a jacket that is broken many times and embodied in the way of a stretched metal.

This endoprosthesis automatically widens from a smaller insertion lumen to a larger lumen. However, this endoprosthesis has little flexibility and in any case potentially has the hazard of fatigue fractures when implanted via a joint. Not all of the struts forming the jacket are connected with each other in the corner points, and, in the implanted state, such struts may thus detach themselves from the vascular wall and protrude into such a wall.

SUMMARY OF THE INVENTION

Contrary to the above mentioned prior art, it is an object of the present invention to provide an endoprosthesis which, as compared to the stents known according to the state of the prior art, is more flexible and has superior strength and stability in the expanded state.

This object is achieved in accordance with the present invention in that the endoprosthesis is a hose-like netting produced from at least one elastic filament, such netting having the structure of a wire screen fence with mesh forming polygons, in which the filaments each grip around each other in their corner points in the direction of the meshes following one another in the direction of the longitudinal axis of the prosthesis.

An endoprosthesis of the invention, which may be self-expanding by means of a balloon catheter, is adaptable to the requirements in any given application in a simple way, and represents a flexible structure that is implantable without problems also in joint regions and then capable of following the movements of the joint of the patient without impediment. In particular, it has been found that as compared to the prior art, such an endoprosthesis has an enhanced ratio between a small and a large radius in the widened position. This means that the insertion catheter to be inserted during implantation can be kept smaller than possible in connection with known prostheses.

It has been found that it is especially preferable if the hose-like netting forming the endoprosthesis comprises at least one through-extending filament, which is braided into a round shape, forming meshes. Alternatively, the endoprosthesis can be produced from an initially flat netting that is then rolled into a hose shape, whereby two longitudinal edges of the netting are then joined with each other by means of a longitudinal seam.

According to a particularly preferred embodiment of the invention, provision is made that the filaments loosely grip around each other, in each of the meshes adjacent to each other in the longitudinal direction of the prosthesis. In this manner, the prosthesis can be shortened from its maximum length so that the filaments will be abutting each other in the corner points of the meshes, by pushing the meshes together.

With such an embodiment, the endoprosthesis is one that can be changed in its length within predetermined limits, whereby in the case of maximum axial expanse, the filaments gripping around each other abut one another in the corner points of the meshes. On the other hand, in the case of a shortening, these filaments grip around each other with more or less axial play. The special advantage of such an embodiment of the prosthesis is that whenever the length is adjusted to a length smaller than the maximum length, no shortening occurs during widening because the material required for widening in the radial direction has not be made available by shortening the length, but is available through the filaments of the individual meshes which do not abut one another axially.

Furthermore, it has been found that it is desirable if the filaments are provided in the corner points of the meshes with interlocks engaging one another in a form-locked way. Such interlocks provide the prosthesis with a particularly pronounced strength in its widened condition.

The aforementioned interlocks may be depressions formed by compressing the filaments intersecting each other in the stretched condition of the prosthesis in the corner points to approximately the thickness of one filament. These depressions engaging each other in the stretched condition of the prosthesis in a form-locked way in their locking positions, thereby provide a form-closed lock in each corner point.

Instead of having the filaments loosely gripping around one another in the corner points of the meshes forming polygons, it is possible also to provide an embodiment in which, in the corner points of the meshes following each other in the direction of the longitudinal expanse of the prosthesis, the filament of each mesh is looped around the filament of the other mesh, forming an eye. Naturally, reducing the length of an endoprosthesis so formed by axial compression is limited, as compared to the embodiment with filaments that loosely grip around each other in the corner points.

According to another embodiment, provision is made that the filaments crossing each other in the corner points of the meshes are connected with each other, which means that the points of intersection are stabilized in this way. This naturally leads to a comparatively high stiffness of such an endoprosthesis. Stabilization can be realized in many different ways, for example by gluing, fusing or soldering of the filaments at the points of intersection. Also, at the points of intersection, the filaments can be enclosed by clips or joined with each other by clamping such filaments together.

An additional embodiment for achieving the object of the invention is one in which the endoprosthesis is a hoselike netting produced from elastic filaments, such netting having the structure of a mesh wire fence with meshes forming polygons, and that the meshes each have connection zones with two filaments twisted around each other, such zones of connection extending in the longitudinal direction of the prosthesis.

An endoprosthesis with the above features is characterized by a particularly pronounced strength and stability in the expanded widened state without impairing the flexibility of the hoselike netting.

In such an endoprosthesis, the connection zones comprising two filaments twisted around each other extend in the longitudinal direction of the prosthesis. According to a further embodiment, the connection zones can also extend along—imaginary—screw thread-like lines of an also imaginary cylinder jacket extending from the prosthesis, forming a helix structure. In this connection, the arrangement also may be selected in such a way that the helix structure is broken by changing the direction of successive meshes in a way such that with part of the meshes, the connection zones extending between such meshes extend at an angle relative to the zones of connection between other meshes, which leads to a structure as found in connection with "fish scales".

With such an endoprosthesis, meshes adjacent each other in the circumferential direction each can be formed by two filaments, and meshes following each other in the axial direction as well as meshes joined with each other in each case via a connection zone each can be formed by the same two filaments. Alternatively, meshes disposed adjacent to each other in the circumferential direction each can be formed by two filaments, and the meshes disposed adjacent to each other axially and in the circumferential direction each can be formed by one of these filaments and another filament. Thus, the filaments participate in the axial direction and progressively from one mesh to the next in the formation of meshes disposed adjacent to each other in the circumferential direction, extending one after the other around the stent in the way of stairsteps. Such a formation of the stent has been found to be easily producible and to be advantageous with respect to its strength and stability in the widened state.

Another preferred embodiment of the invention is characterized in that in the corner points of the meshes disposed radially adjacent to each other, the filaments each are twisted around against each other with a winding in a way such that under axial tensile forces, the locks formed by the twistings become disengaged, and the prosthesis, when losing its radial bearing strength, undergoes a lengthwise expansion as well as a change in cross section, leading to a small lumen.

An endoprosthesis so formed can be advanced with a small cross section and corresponding longitudinal expanses without problems, for example in a blood vessel, by means of a suitable catheter, and subsequently brought into its functional position by radial widening associated with predetermined shortening.

Furthermore, with such an embodiment, the filaments can be provided with depressions engaging each other form-locked in the expanded state, by pressing them together in the zones of connection, such zones being twisted against each other, which, in the widened state, results in superior locking and thus in greater radial bearing strength and stability.

According to another embodiment, provision is made that one filament extends in each case without twisting in the connection zones in the longitudinal direction of the prosthesis, and that the other filament is wound around this filament in the form of a spiral. Such an embodiment permits a limited sliding of the one filament along the straight-lined section of the other filament, and, in view of the spiral-like windings, also permits a compression and stretching of the one filament. This permits a superior adaptation of an endoprosthesis so formed within curved areas.

Another further embodiment includes a lock with at least one retaining bar, which extends in the longitudinal direction of the prosthesis and is solidly anchored in the netting with its one end, as well as provided on the other end with a hook for engaging a mesh. During radial widening of an endoprosthesis fitted with such a lock, the end of the retaining bar fitted with the hook slides across the meshes as the prosthesis is radially widened and the netting is shortened at the same time. The hook grips behind the filaments of the mesh, with the result that following the widening, the hose-like netting is prevented from radial compression in that any increase in length caused by a radial reduction is no longer possible.

Desirably, the retaining bar can extend along the hose-like netting on the outer side and, in the implanted state, thus can be received between a vascular wall and the hose-like netting. It is assured in this way that no impairment of the lumen will occur under any circumstances. However, the retaining bar may also extend through the meshwork of the netting in the way of a warp thread, which keeps the lumen free as well.

According to another preferred embodiment of the second variation of the invention, provision is made that the meshes comprise through-extending first filaments and second filaments connecting the first ones with each other. The second filaments are each wound around the first filaments by one mesh length and project at the end of the respective mesh to an adjacent first filament, and are wound again around the adjacent first filament again across one mesh length, and again project to another first filament at the end of the respective mesh. Thus, this type of mesh formation continues and the second filaments, upon winding around a first filament, each extend around an imaginary cylinder jacket of the endoprosthesis in a progressively, stair-step manner.

With a further development of the two embodiment variations explained above, it is desirable to provide for limiting the length of the stent, the hose-like netting is fitted with warps extending in the longitudinal direction of the stent, which warps may be connected with the filaments forming the meshes at least within the zone of the ends of the prosthesis. These warp threads may include textile filaments and may be arranged closely adjacent to each other in a way such that they form a jacket enclosing the stent.

According to a further embodiment of the last-mentioned feature, the warp threads may include biodegradable material and/or may be designed as medication depots, releasing medications in the course of their degradation. An example of such a biodegradable material is vegetable fiber or animal fiber.

According to yet another further embodiment, provision is made that the warp threads include extensible material such as textured textile threads. However, the warp threads may also include nonelastic material having a high density and proton number, which has been found to be particularly advantageous in connection with implantations under X-ray control because such a material absorbs X-rays to a high degree and is, therefore, highly visible in the X-ray image. Examples of such materials include titanium wire or stainless steel wire.

The filaments, whether first or second, can be made from biocompatable materials, such as polyamide fibers like nylon fibers or polyolefin fibers such as polyethylene fibers or polypropylene fibers. These fibers have a diameter which ranges between 0.01 mm and 1.0 mm.

Desirably, with the two embodiment variations discussed above, the ends of the filaments are bent off and joined with the netting at the face ends of the hose-like netting as well, in order to effectively avoid injury in the course of implantation, or in the implantation site. For example, the bentoff ends of the filaments may be braided in, glued, soldered or fused at the face ends of the hose-like netting, or also may be shaped as eyes.

According to another embodiment of these two variations, which is important as well, provision is made that the filaments forming the meshes of the hose-like netting are rounded off or flattened on the side facing the lumen, in order to obtain favorable properties of flow on the inside wall of a vessel receiving such an endoprosthesis. The term "lumen" refers to a blood vessel.

Finally, it has been found to be desirable if in connection with these two embodiment variations, the filaments forming the netting are comprised by a superelastic material, or a memory material, for example such as nitinol.

Within the framework of the present invention, both embodiment variations can be realized in the form of balloon-expandable or also self-expanding endoprosthesis.

Other objects and features of the present invention will become apparent from the following detailed description considered in connection with the accompanying drawings which discloses several embodiments of the present invention. It should be understood, however, that the drawing is designed for the purpose of illustration only and not as a definition of the limits of the invention.

BRIEF DESCRIPTION OF THE DRAWINGS

In the drawings, wherein similar reference characters denote similar elements throughout the several views.

DETAILED DESCRIPTION OF PREFERRED EMBODIMENTS

Figure 1:
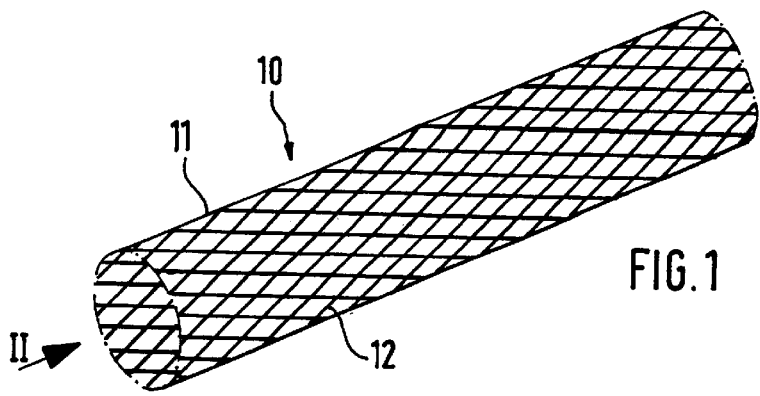
FIG. 1 shows a perspective view of an endoprosthesis in the form of a hose-like netting having the structure of a wire mesh fence.
Figure 2:
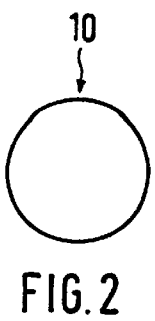
FIG. 2 shows an end view of the endoprosthesis viewed in the direction of arrow II in FIG. 1.
Figure 3:
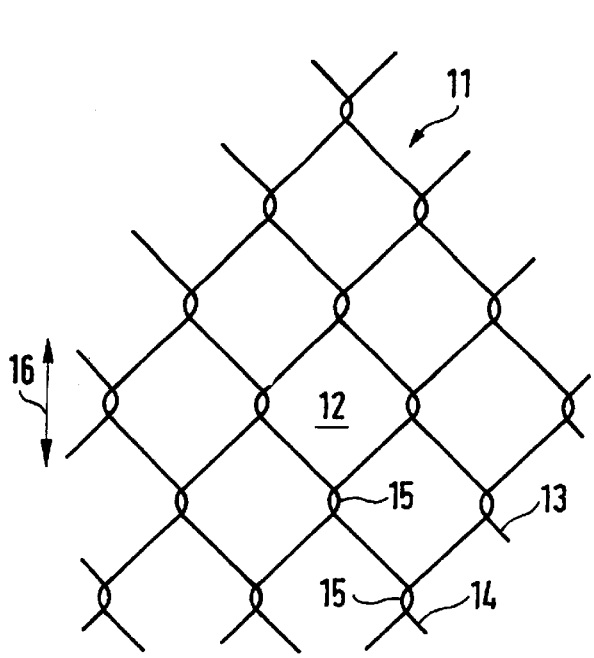
FIG. 3 shows a cutout-like unwinding of the prosthesis jacket illustrating the structure of the netting comprising filaments forming polygons, such filaments not being joined at the respective points of intersection.
Figure 4:
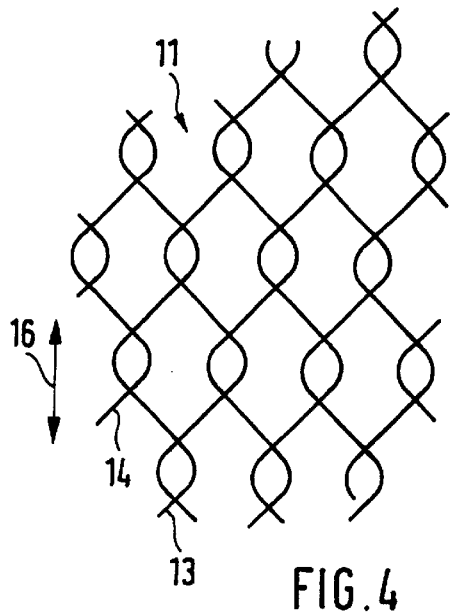
FIG. 4 shows the netting as seen in FIG. 3; however, with the prosthesis being in an axially compressed state.

Turning now in detail to the drawings, the endoprosthesis 10 illustrated in FIGS. 1 to 4 is comprised of a hose-like netting 11 with the meshes 12 forming polygons. These meshes are formed by the filaments 13, 14, which grip around each other at the corner points 15 without any fixed connection; and these filaments are the ones of the meshes disposed adjacent to each other in the longitudinal direction of the prosthesis. Especially FIGS. 3 and 4 where the endoprosthesis is shown unwound. illustrate the wire mesh fence-like structure of the netting 11, whereby the arrow 16 indicates the bearing direction, the latter extending transversely to the longitudinal axis of the prosthesis. FIG. 3 shows the mesh pattern, with filaments adjacent each other at each of the corner points 15 with maximum lengthwise expansion of the prosthesis 10. FIG. 4 shows the mesh pattern of an axially compressed prosthesis, in which the filaments 13, 14 grip around each other at the corner points with much play. The term "mesh" or "meshes" refers to the actual cord or wire network, and not the spaces therebetween.

The prosthesis 10 according to the invention may be either self-widening or balloon-expandable, whereby no axial reduction during widening occurs at all if the prosthesis is made shorter in the unexpanded condition versus its maximum lengthwise expansion, and approximately has a mesh pattern according to FIG. 4. If the filaments 13, 14 grip around each other at the corner intersection points 15 without play with maximum expansion of the prosthesis lengthwise, in the manner as shown in FIG. 3, then the radial widening naturally leads to a reduction in length. On the other hand, if such a prosthesis is axially compressed prior to its expansion widening in accordance with the mesh pattern according to FIG. 4, then no reduction at all in length occurs during widening, which means that exact positioning is assured at the site of the implantation.

FIGS. 3 and 4 show that the filaments 13, 14 grip around each other at the corner points of the polygon forming meshes 12 where these corner points are adjacent with respect to the longitudinal direction of the prosthesis. The corner points are adjacent to each other. This construction for the endoprosthesis is the precondition for its radial bearing strength, which is indicated by the arrow 16 between the FIGS. 3 and 4. Arrow 16 is directed transversely to the longitudinal axis of the prosthesis.

Figure 6:
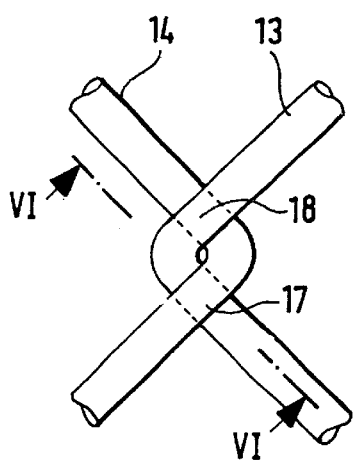
FIG. 6 shows a section view through an intersection zone, with this section taken along section line VI—VI in FIG. 5.
Figure 5:
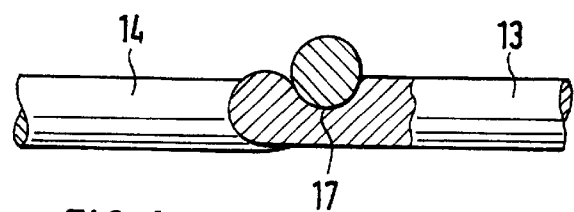
FIG. 5 shows an intersection zone of the filaments, and these filaments being provided with locks engaging each other in a form-locked way, with maximum expansion lengthwise.

An enhancement of the radial bearing strength of the prosthesis of the invention is achievable if the filaments forming the meshes are provided at the points of intersection with locks engaging each other in an interlocking manner. FIGS. 5 and 6 show that with maximum longitudinal expansion of the length of the prosthesis, the filaments 13, 14 intersecting each other at the corner points 15 of the polygons are compressed crosswise relative to the longitudinal expanse of the prosthesis in such a way that each filament is received in an interlocking way in a depression 17, 18 of the other filament. Thus, both filaments are jointly reduced to the thickness of about one filament and hooked into each other as a result of the interlocking engagement, thereby providing an enhancement of the radial bearing strength of the endoprosthesis.

Figure 7:
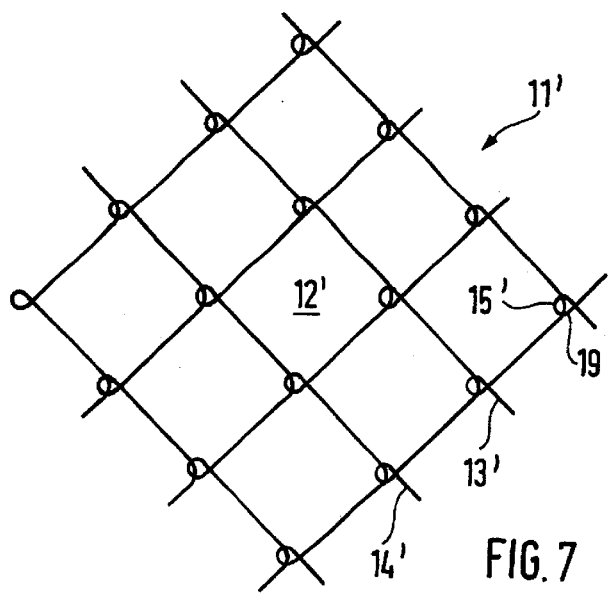
FIG. 7 shows, in a view similar to FIG. 3, a second embodiment for the structure of the prosthesis, with a netting where, in the corner points of the meshes following each other in the direction of the longitudinal expanse of the prosthesis, the filament of each mesh is looped around the filament of the other mesh, forming an eye.

In the embodiment according to FIG. 7, the netting 11' forming the endoprosthesis differs from the netting 11 according to FIG. 3 only in that in the points of intersection 15' of the filaments 13', 14', only one of the filaments is looped around the other filament, forming an eye 19. The radial bearing strength is increased by this embodiment as well; however, as opposed to the embodiment according to FIG. 3, no shortening is possible by axial compression.

Figure 8:
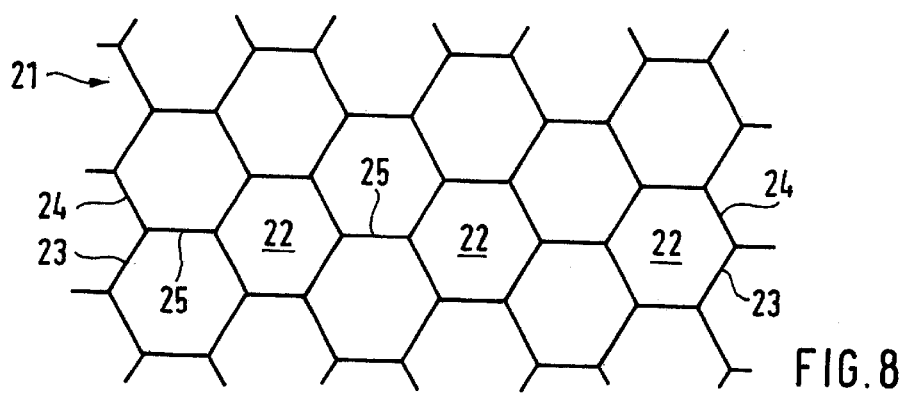
FIG. 8 shows in a view similar to FIG. 7 another embodiment of the netting.

The jacket of an endoprosthesis as shown in unwound manner in FIG. 8 in a cutout view relates to a netting 21 in which the meshes 22 are designed as hexagons and separated from each other, both by filaments 23, 24 and by connection zones 25 where said filaments extend in an oblique angle with respect to the longitudinal axis of the prosthesis and said connection zones extend parallel to said longitudinal axis. In each of said connection zones, two filaments 23, 24 are twisted with each other. Such twistings form locks engaging each other in an interlocking way, which locks, in the radially expanded state, provide an endoprosthesis formed by said netting 21 with its strength and stability in the widened condition.

The twistings of the filaments 23, 24 participating in the formation of the meshes are shaped in the connection zones 25 in such a way that they engage one another when the prosthesis is in the widened condition, thereby securing the prosthesis in its widened position, but disengage from each other when axial tensile forces are applied to the prosthesis, thereby permitting a reduction of the cross section of the prosthesis to a Comparatively small lumen.

Accordingly, this prosthesis is an endoprosthesis expandable by means of a balloon catheter. The endoprosthesis is received on the balloon section of the catheter with suitable expanse lengthwise, and with radial widening upon implantation, for example in a blood vessel, undergoing a corresponding axial shortening until the twistings looping around one another lock in an interlocking manner.

Figures 9, 10:
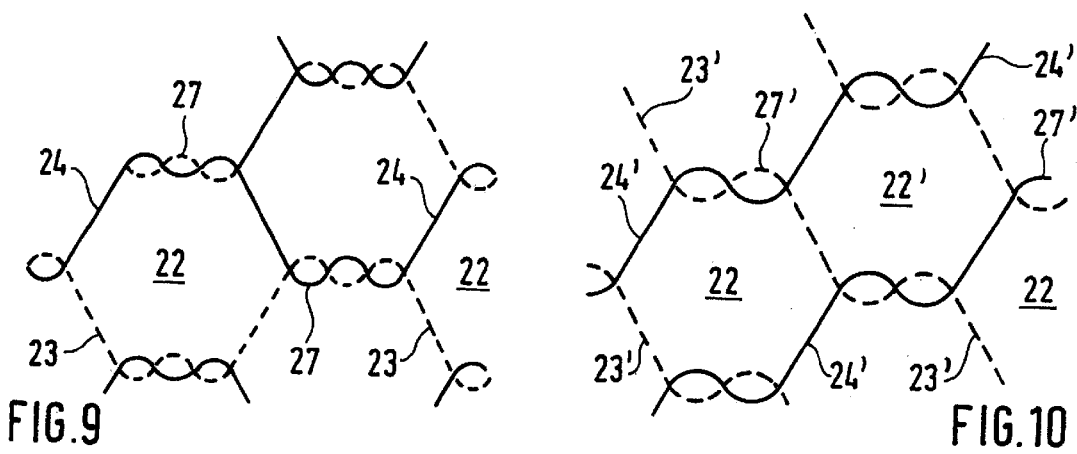
FIG. 9 shows, in an enlarged cutout view from FIG. 8, the formation of meshes each comprising two filaments, such meshes following each other in the longitudinal direction of the prosthesis.
FIG. 10 shows, in a view similar to FIG. 9, a mesh formation in which the filaments are braided one after the other around the endoprosthesis and participate in the formation of meshes, the meshes being disposed adjacent to each other in the longitudinal and circumferential directions.

In connection with the netting 21 illustrated in an enlarged cutout view in FIG. 9, the meshes following each other in the longitudinal direction of the prosthesis each are formed by the same two filaments 23, 24. Accordingly, the two filaments extend from their connection zones 25, 25', (FIGS. and 12) respectively, with an angle of about 60° outwardly to the connection zones between the circumferentially adjacent meshes 22, and from these connection zones back again to a connection zone with the mesh following in the longitudinal direction of the prosthesis. This is shown in FIG. 9 by the filament 24, represented by the fully drawn lines, on the one hand, and by the filament 23 represented by the dashed lines, on the other hand. The connection zone 25 with the twistings 27 forming the locks in the expanded state is shown as well.

Figure 11:
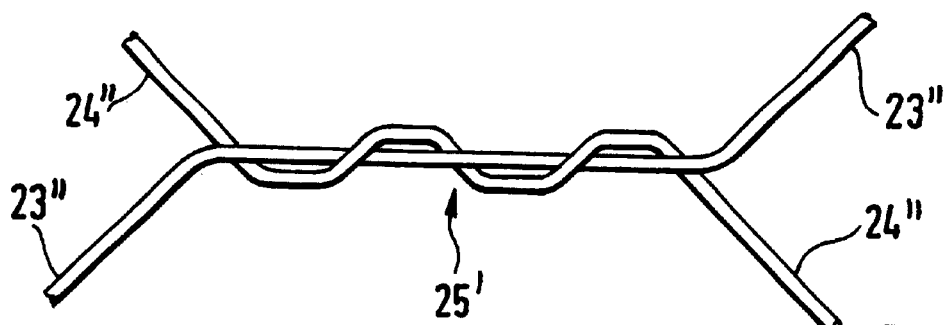
FIG. 11 shows, as an alternative to FIG. 10, an enlarged view of a cutout from a connection zone, in which the one filament extends in a straight line in the longitudinal direction of the prosthesis, and the other filament is wound around said filament.

With the embodiment according to FIG. 10, on the other hand, the filaments 23', 24' in each case form the meshes 22 not following one another in the longitudinal direction of the prosthesis, but the filaments participate progressively from one mesh to the next in the formation of the meshes 22', the latter being disposed adjacent to each other in a direction, that extends helically along the length of the prosthesis. Accordingly, the individual filaments are progressively braided around the hose-like netting from one mesh to the next in the longitudinal direction of the prosthesis. These patterns and the connection zones 27' provided with the twistings forming locks are shown by the filaments represented by fully drawn lines, on the one hand, and dashed lines on the other hand as well. the embodiment according to FIG. 11, the filament 23" extends in the connection zone 25' in a straight line, and the filament 24" is spirally wound around the filament 23". In this way, the filament 24" is capable of sliding to a limited extent on the straight-lined section of the filament 23" and also of undergoing a compression or stretching within predetermined limits. This endoprosthesis consequently is characterized by excellent flexibility and, furthermore, imparts superior adaptation in regions of flexion.

Figure 12:
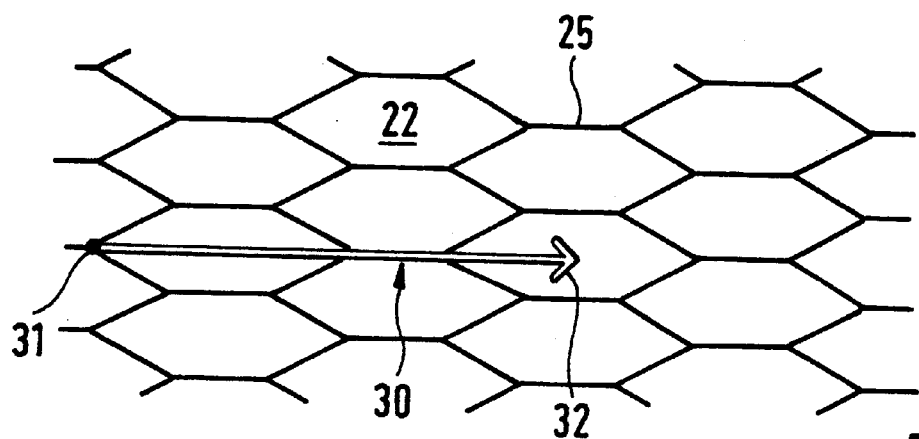
FIG. 12 shows, in a view similar to FIG. 8, a cutout of the netting of an unexpanded endoprosthesis, with a retaining bar extending in the longitudinal direction of the prosthesis.
Figure 13:
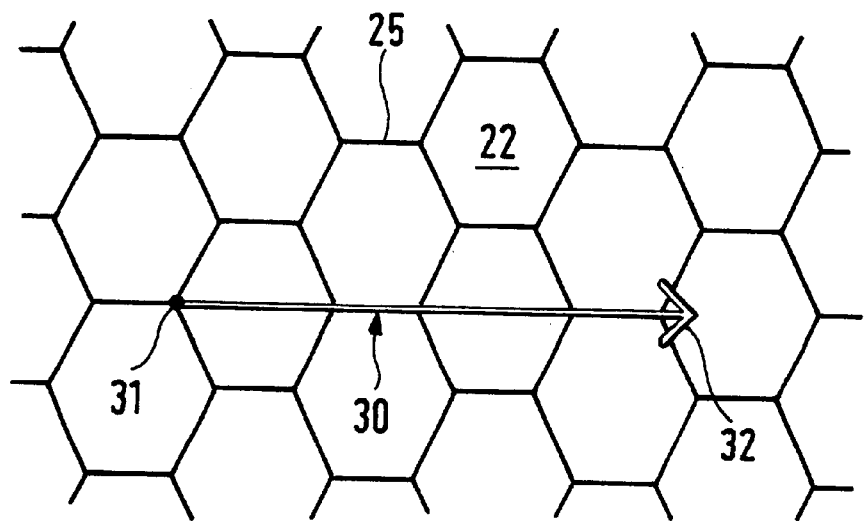
FIG. 13 shows the netting according to FIG. 12 in the expanded condition, in which it is locked in the widened state by means of the retaining bar.

FIGS. 12 and 13 show a netting as illustrated in FIG. 8, with FIG. 12 showing the unexpanded state, whereas FIG. 13 illustrates the widened condition. However, as opposed to the embodiment shown in FIG. 8, in the embodiment according to FIGS. 12 and 13, provision is made for special locking means in the form of at least one retaining bar 30 extending in the longitudinal direction of the prosthesis, such bar being rigidly connected at its one end and—at 31—with the meshwork forming the netting, whereas the other end of the retaining bar has a hook 32. This retaining bar may, extend on the outside along the netting forming the endoprosthesis, or through the meshwork in the way of a warp thread.

When radial expansion occurs from the condition with a small lumen as illustrated in FIG. 12, the hook 32 slides across the meshes due to the reduction in length correspondingly occurring with such expansion, and, in the way as shown in FIG. 13, grips behind the filaments of the mesh, which, following widening, effectively prevents the length from increasing again, and thus any reduction in cross section.

With the endoprosthesis according to FIG. 8, the connection zones 25 are each comprised by two filaments 23, 24, which are twisted with each other and extend in the longitudinal direction of the prosthesis. However, in the embodiment according to FIG. 14, the connection zones 35, 35'— the latter being twisted with each other—are partly arranged obliquely relative to a longitudinal axis of the prosthesis, and accordingly extend like a screw thread around an imaginary cylinder jacket of the prosthesis partly the connection zones 35, 35' are aligned with an angle relative to the first-mentioned connection zones. Due to such change in direction of the connection zones, the helix structure is changed.

Figure 14:
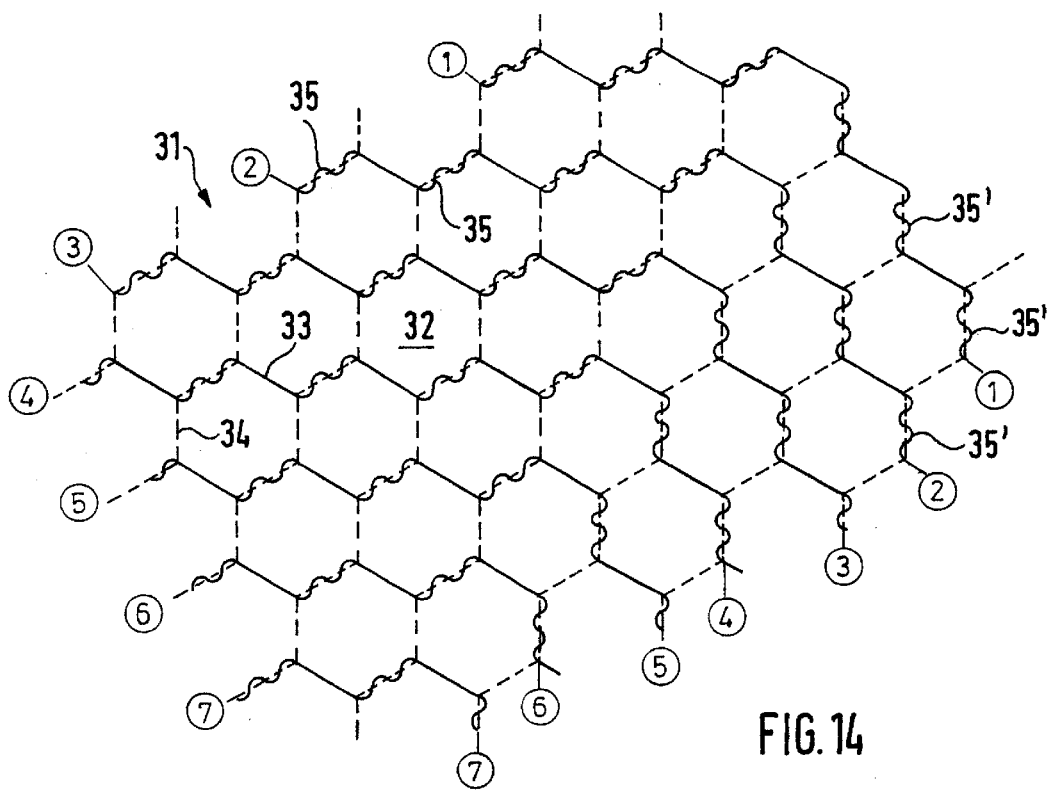
FIG. 14 shows, in a view similar to FIG. 8, a prosthesis structure with a mesh wire fence-like netting, in which the sections of connection between adjacent meshes extend—on the one hand—around an imaginary cylinder jacket in the form of a screw thread, extending inclined relative to the longitudinal axis of the prosthesis, and change the direction, on the other hand, so that a fish scale-like structure is formed.

FIG. 14 shows the filaments 33 by the fully drawn lines, whereas the other filaments 34 are shown by the dashed lines. The course followed by the filaments 33 shown in the drawing by the fully drawn lines is indicated by the numerals 1 to 7 associated with said filaments. The filaments 33 each form with a filament 34 a plurality of connection zones 35 between the adjacent meshes 32, such zones extending inclined relative to the longitudinal axis of the prosthesis, and at an angle relative to the latter the connection zones 35' extending approximately at right angles relative to the longitudinal axis of the prosthesis. The connection zones 35' consequently extending in the circumferential direction on the imaginary cylinder jacket of the prosthesis.

The connection zones 35 are arranged in one direction which is oblique to the longitudinal and all of the connection zones 35' are arranged in the circumferential direction.

Figure 15:
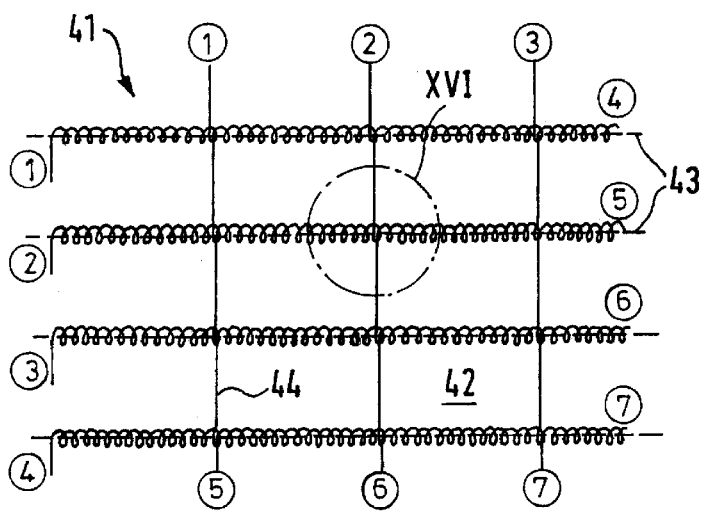
FIG. 15 shows a prosthesis structure with rectangular meshes.
Figure 16:
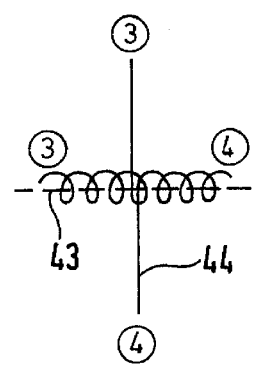
FIG. 16 shows in the cutout according to XVI from FIG. 15 which is an enlarged corner point between adjacent meshes.

The embodiment according to FIGS. 15 and 16 relates to a prosthesis with the rectangularly shaped meshes 42, which are comprised by the first filaments 43 extending parallel with each other in the longitudinal direction of the prosthesis, and the second filaments 44, the latter being wound around the first filaments 43. The filaments 43 are shown in the drawing by the dashed lines and the second filaments 44 by the fully drawn lines.

In this connection, the arrangement is selected in such a way that the second filaments 44 each are wound around a second, through-extending filament 43, and then project at the end of a mesh 42 to the adjacent, through-extending filament 43, and are again looped around the latter in the longitudinal direction of the prosthesis. Thus the second filaments 44 progress, extending around the jacket of the prosthesis in the form of stairsteps in the longitudinal direction of the prosthesis. For the purpose of illustrating the course of the second filaments 44 shown by the fully drawn lines, the numerals 1 to 7 are associated with said filaments.

FIG. 16 illustrates in an enlarged cutout view a through extending first filament 43, around which a second filament 44 is wound up to the corner point of the meshes 42 disposed adjacent to one another, such second filament then extending further to an adjacent filament. The filament 44 is denoted by the numeral 3. Another second filament 44, which is denoted by the numeral 4, meets with the first filament 43 in the corner point shown, and is twisted with the latter, in order to then project at the end of the mesh 42 in the circumferential direction to the next through-extending filament 43.

While several embodiments of the present invention have been shown and described, it is to be understood that many changes and modifications may be made thereunto without departing from the spirit and scope of the invention as defined in the appended claims.

What is claimed is:

1. Endoprosthesis percutaneously implantable by means of a catheter in a body of a patient, comprising:

an oblong, hollow body having a longitudinal axis and which, upon placement in a position during implantation, is changeable from a small lumen during insertion to a larger lumen that conforms to a functional position of the endoprosthesis;

wherein said endoprosthesis is a cylindrical netting produced from elastic filaments, such netting having meshes forming polygons with sides, the meshes further having connection zones with two filaments twisted around each other such that the two filaments are sides of the polygons, the polygons having sides that extend, at least in part, obliquely to the longitudinal axis; and the endoprosthesis having a plurality of meshes each with a first connection zone and a second connection zone such that the first connection zone extends at an inclined angle relative to the longitudinal axis of the endoprothesis and the second connection zone extends at a different angle relative to said longitudinal axis than said inclined angle.

2. Endoprosthesis according to claim 1, wherein the connection zones have two filaments, and said filaments are twisted around each other along a connection zone axis that extends at an inclined angle relative to the longitudinal axis.

3. Endoprosthesis according to claim 1, wherein there is a connection zone, which has a first filament helically twisted around a second filament.

4. Endoprosthesis according to claim 1, wherein adjoining meshes along the longitudinal axis are connected with a connection zone formed by two filaments.

5. Endoprosthesis according to cl wherein at ends of the netting, the ends of the filaments are joined by being braided, glued, soldered or fused.

6. Endoprosthesis according to claim 1, wherein the filaments forming the meshes of the netting are shaped rounded or flattened on a side adjacent the lumen.

7. Endoprosthesis according to claim 1,
wherein the filaments forming the netting comprise superelastic material.

8. Endoprosthesis according to claim 1,
wherein said polygons of the meshes are hexagons.

9. An endoprosthesis implantable in a body of a patient, comprising:
an oblong, hollow body having a longitudinal axis, said endoprosthesis being a cylindrical netting of elastic filaments, such netting including meshes forming hexagons having sides, each mesh having connection zones with two filaments helically twisted around each other; and
said endoprosthesis having a first plurality of meshes each with a first connection zone inclined at an angle relative to the longitudinal axis of the mesh and a second connection zone that is parallel to the first connection zone.

10. The endoprosthesis of claim 9, wherein the connection zones have two filaments, and said filaments are twisted around each other to form a side of a hexagon.

11. The endoprosthesis of claim 9, further comprising a second plurality meshes with a connection zone extending orthogonal to the longitudinal axis.

12. The endoprosthesis of claim 9, wherein the meshes adjoining each other along the longitudinal axis are connected with each other with a connection zone formed by helically twisted filaments.

13. The endoprosthesis of claim 9, wherein at ends of the hose-like netting, ends of the filaments are bent off and joined with the netting, the ends of the filaments being braided, glued, soldered or fused.

14. The endoprosthesis of claim 9, wherein the filaments forming the meshes of the tube shaped netting are shaped rounded or flattened on a side adjacent the lumen.

15. The endoprosthesis of claim 9, wherein the filaments forming the netting comprise superelastic material.

16. An endoprosthesis implantable in a body of a patient, comprising:
an oblong, hollow body having a longitudinal axis, said endoprosthesis being a cylindrical netting of elastic filaments, such netting including meshes forming polygons having sides, each mesh having connection zones with two filaments helically twisted around each other; and
said endoprosthesis having a first plurality of meshes each with a first connection zone inclined at a first angle relative to the longitudinal axis of the endoprosthesis and a second plurality of meshes each with a connection zone inclined at a second angle relative to the longitudinal axis of the endoprosthesis such that the second angle is different from the first angle.

17. The endoprosthesis of claim 16, wherein the connection zones have two filaments, and said filaments are helically twisted around each other to form a side of a hexagon.

18. The endoprosthesis of claim 16, wherein the second plurality of meshes have connection zones, extending orthogonal to the longitudinal axis.

19. The endoprosthesis of claim 16, wherein the meshes adjoining each other along the longitudinal axis are connected with each other via a connection zone formed by the filaments from the adjoined meshes.

20. The endoprosthesis of claim 16, wherein at ends of the hose-like netting, ends of the filaments are bent off and joined with the netting, the ends of the filaments being braided, glued, soldered or fused.

21. The endoprosthesis of claim 16, wherein the filaments forming the meshes of the tube shaped netting are shaped rounded or flattened on a side adjacent the lumen.

22. The endoprosthesis of claim 16, wherein the filaments forming the netting comprise superelastic material.

* * * * *